United States Patent [19]

Green et al.

[11] Patent Number: 5,399,572
[45] Date of Patent: Mar. 21, 1995

[54] CHLORMETHIAZOLE IN THE TREATMENT OF NEURODEGENERATION

[75] Inventors: Alfred R. Green, Oxon; Alan J. Cross, Surrey; Bernard R. Boar, Hertfordshire, all of Great Britain

[73] Assignee: Aktiebolaget Astra, Sodertalje, Sweden

[21] Appl. No.: 84,764

[22] Filed: Jun. 28, 1993

Related U.S. Application Data

[63] Continuation of Ser. No. 743,397, Aug. 15, 1991, abandoned.

[30] Foreign Application Priority Data

Feb. 17, 1989 [SE] Sweden .................. 8900654

[51] Int. Cl.[6] .................................... A61K 31/425
[52] U.S. Cl. ........................................... 514/365
[58] Field of Search ................................ 514/365

[56] References Cited

FOREIGN PATENT DOCUMENTS 20230370 1/1987 European Pat. Off. .

OTHER PUBLICATIONS

M. Ende, et al., Urinary Metabolites of Clomethiazole, *Arzneim-Forsch/Drug. Res.* 29 (II) Nr. 11, pp. 1655–1658 (1979).
R. Pal, et al., Thiomethylation and Thiohydroxylation-A New Pathway of Metabolism of Heterocyclic Compounds, *Xenobiotica*, vol. 12, No. 12, pp. 813–820 (1982).
C. P. Offen, et al., 4,5-Dimethylthiazole-N-Oxide-S-Oxide; A Metabolite of Chlormethiazole In Man, *Xenobiotica*, vol. 15, No. 6, pp. 503–511 (1985).
A. R. Green, et al., A Simple Intravenous Infusion Method In Rodents For Determining the Potency of Anticonvulsants Acting Through GABAergic Mechanisms, *J. Pharm. Pharmacol.* 41; 879–800 (1989).
Goodman and Gilman's *The Pharmacological Basis of Therapeutics* Seventh Edition, pp. 13, 357, 454 and 455 (1985).
D. V. Parke, *Recent Advances In Pharmacology*, 4th Ed., p. 68, (1968) reprinted In Taylor et al. *Introductory Medicinal Chemistry*, p. 182.
Alfred Burger, *A Guide To The Chemical Basis of Drug Design*, p. 137 (1983).
Paul L. Ornstein, et al., Synthesis and Pharmacology Of A Series of 3- and 4-(Phosphonoalkyl)Pyridine-And-Piperidine-2-Carboxylic Acids. Potent N-Methyl-D-Aspartate Receptor Antagonists, *J. Med. Chem.* 32, 827 (1989).
C. W. Cotman et al., Excitatory Amino Acids In The Brain—Focus On NMDA Receptors, *TINS*, vol. 10, No. 7, pp. 263–265 (1987).
William F. Maragos, et al., Glutamate dysfunction in Alzheimer's disease: an hypothesis, *TINS* 10, 65–68 (1987).
N. T. Gurusinghe, et al., Chlormethiazole In The Management Of Post-Cranitomy Seizures, *Acta. Psychiatr. Scand. Suppl.* 329, vol. 73, pp. 189–193 (1986).
S. A. Ather, et al., A Comparison Of Chlormethiazole And Thioridazine In Agitated Confusional States Of The Elderly, *Acta. Psychiatr. Scand. Suppl.* 329, vol. 73, pp. 81–91 (1986).
T. V. Stanley, Oral Chlormethiazole In Childhood Epilepsy, *Archives Of Disease In Childhood*, vol. 57, pp. 242–243 (1982).

(List continued on next page.)

*Primary Examiner*—Raymond J. Henley, III
*Assistant Examiner*—Phyllis G. Spivack
*Attorney, Agent, or Firm*—White & Case

[57] ABSTRACT

A thiazole of the following formula is disclosed

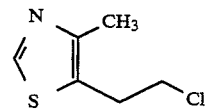

for the treatment of neurodegeneration involving loss of neuronal structure.

7 Claims, No Drawings

OTHER PUBLICATIONS

Louis Low et al., Prolonged Intravenous Use of Chlormethiazole (Heminevrin), *British Medical Journal*, p. 484 (1980).

F. Nouailhat et al., abstract of Treatment of Status Epilepticus In The Adult, *Rev. Electroencephalogr. Neurophysiol Clin.* 14, 237 (1985).

C. Carlsson et al., Influence of Chlormethiazole On Cerebral Blood Flow and Oxygen Consumption In The Rat, And Its Effect On The Recovery of Cortical Energy Metabolism After Pronounced, Incomplete Ischaemia, *Acta. Anaesth. Scand.* 23, 259–266 (1979).

M. G. Mead et al., Confusion And Hypnotics In Demented Patients, *Journal Of The Royal College Of General Practitioners* 32, 763–765 (1982).

Chemical Abstract 66: 45369f (1967).

Chemical Abstract 79: 40671g (1973).

CHLORMETHIAZOLE IN THE TREATMENT OF NEURODEGENERATION

This application is a continuation of application Ser. No. 07/743,397, filed on Aug. 15, 1991, now abandoned.

SUMMARY OF THE INVENTION

This invention relates to a new medical use for a heterocyclic compound and pharmaceutical compositions containing it. In particular, it relates to the use of 5-(2-chloroethyl)-4-methylthiazole and the pharmaceutically acceptable salts and solvates thereof, in the prevention and/or treatment of neurodegeneration in pathological conditions such as stroke, cerebral ischaemia, hypoxia, epilepsy and neurodegenerative diseases such as Alzheimer's disease, multi-infarct dementia and Huntington's disease. This thiazole compound with which the present invention is concerned has the following structural formula

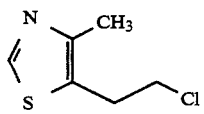

and is known alternatively as chlormethiazole, chlomethiazole or chlorethiazole.

BACKGROUND TO THE INVENTION

Preparations containing chlormethiazole, particularly in the form of its acid addition salts, especially, as disclosed in GB 847,520, the acid addition salt with ethanedisulphonic acid, are known to possess valuable therapeutic properties. The general pharmacology and therapeutic applications of chlormethiazole have been extensively reviewed in a recent publication (Acta Psychiatr. Scand., Suppl. 329, 73, 1986). Thus, for example, chlormethiazole possesses sedative and hypnotic properties and is used clinically as a hypnotic in the elderly, particularly in the management of psychogeriatric patients. Chlormethiazole also possesses anticonvulsant properties and is used clinically for the treatment of different types of convulsive states, such as, for example, status epilepticus and pre-eclampsia. Chlormethiazole is also used clinically for the treatment of ethanol (alcohol) withdrawal states including delirium tremens.

The present invention can be distinguished from the above prior art in that it is concerned with a new medical use which is unexpected and which can be clearly distinguished from the applications in the above described disorders. Usefulness in any or all of the above clinical disorders would not suggest or in any way make obvious the use of the compounds which are the subject of the present invention in the prevention and/or treatment of neurodegeneration.

There are a few contradictory reports on the effects of chlormethiazole on cerebral circulation and metabolism. I. Pichlayr and co-workers (Anaesthesist, 1973, 22, 496–500) found that i.v. infusion of chlormethiazole into dogs caused an initial increase in cerebral blood flow, followed by a decrease in both cerebral blood flow and oxygen consumption rate, a finding which they interpreted as indicating that chlormethiazole possibly offers a degree of protection to cerebral functions. Others (J. Pogady, M. Ruscak and J. Orlicky, Activ. Nerv. Sup. (Prague), 1972, 14, 87) have presented results which are interpreted as possibly indicating a deleterious effect of chlormethiazole in situations associated with impaired brain circulation. Significantly, in the most recent study (Acta Anaesth. Scand., 1979, 23, 259–266) Carlsson and Rehncrona were unable to demonstrate either a protective or a detrimental effect of chlormethiazole when it was administered during reversible, incomplete ischaemia in the rat. None of the above studies considered an action of chlormethiazole on neurodegeneration following pathological insult.

The present invention provides a method for the prevention and/or treatment of neurodegeneration in the above mentioned pathological conditions. Thus the new use of chlormethiazole that is the subject of the present invention could not in any way be expected from the above prior art.

Other compounds have been reported to be useful in the prevention and/or treatment of neurodegeneration (see, for example, EP 230 370 and EP 273 309), but there is no drug that is presently accepted as a standard for this use. None of the other compounds thus described would suggest the use of the compound of the present invention for the prevention and/or treatment of neurodegeneration.

DETAILED DESCRIPTION OF THE INVENTION

Different aspects of the present invention are:
the use of 5-(2-chloroethyl)-4-methylthiazole, or a pharmaceutically acceptable salt or solvate thereof, in the manufacture of a medicament for the prevention and/or treatment of neurodegeneration, especially in connection with conditions such as stroke, cerebral ischaemia, hypoxia, epilepsy and in neurodegenerative diseases such as Alzheimer's disease, multi-infarct dementia and Huntington's disease;

a method for the prevention and/or treatment of neurodegeneration, especially in connection with conditions such as stroke, cerebral ischaemia, hypoxia, epilepsy and in neurodegenerative diseases such as Alzheimer's disease, multi-infarct dementia and Huntington's disease, comprising administering a sufficient amount of 5-(2-chloroethyl)-4-methylthiazole or a pharmaceutically acceptable salt or solvate thereof;

a pharmaceutical formulation for use in the prevention and/or treatment of neurodegeneration, especially in connection with conditions such as stroke, cerebral ischaemia, hypoxia, epilepsy and in neurodegenerative diseases such as Alzheimer's disease, multi-infarct dementia and Huntington's disease, comprising 5-(2-chloroethyl)-4-methylthiazole as active ingredient.

Pharmaceutically acceptable salts include, besides the said salt with ethanedisulphonic acid, salts with methane polysulphonic acids, ethane monosulphonic acids and ethane polysulphonic acids. The salt with ethanedisulphonic acid is the preferred salt.

The clinically most important of the new fields of use are considered to be the prevention and/or treatment of neurodegeneration in connection with stroke, cerebral ischaemia, multi-infarct dementia and hypoxia.

The effectiveness of 5-(2-chloroethyl)-4-methylthiazole for use according to the present invention in the prevention and/or treatment of neurodegeneration may be demonstrated by the ability to decrease damage to the CA1/CA2 hippocampal pyramidal neurones in gerbils following ischaemia induced by a period of occlusion of the carotid arteries followed by reperfusion. The detailed mechanisms that underlie ischaemia-induced degeneration of hippocampal neurones have yet to be clarified, but the above mentioned gerbil test system has been widely used as a predictive model of neuroprotective activity (see, for example, B. J. Alps, C. Calder, W. K. Hass and A. D. Wilson, Brit. J. Pharmacol., 1988, 93, 877–883; R. Gill, A. C. Foster and G. N. Woodruff, Neuroscience, 1987, 7, 3343–3349).

It is a particular feature that the compound of the present invention is effective in preventing and/or treating neurodegeneration not only when administered prior to the ischaemic insult, but also when administered solely after the ischaemic insult, even several hours after the ischaemic insult. It is to be expected that the efficacy when administered post-ischaemia is of particular relevance to the likely clinical utility.

The administration in the novel method of treatment of this invention may conveniently be oral, rectal, or parenteral at a dosage level of, for example, about 1 to 3000 mg/kg, preferably about 10 to 1000 mg/kg and especially about 25 to 250 mg/kg and may be administered on a regimen of 1 to 4 times per day. The dose will depend on the route of administration, a particularly preferred route being by intravenous infusion of an aqueous solution containing chlormethiazole ethanedisulphonate, for example, an aqueous solution containing chlormethiazole ethanedisulphonate 8 mg/ml. It will be appreciated that the severity of the disease, the age of the patient and other factors normally considered by the attending physician will influence the individual regimen and dosage most appropriate for a particular patient.

The pharmaceutical formulations comprising the compound of this invention may conveniently be tablets, pills, capsules, powders or granules for oral administration; sterile parenteral solutions or suspensions for parenteral administration; or as suppositories for rectal administration.

Neuroprotection Studies

Ischaemia was induced in gerbils by occlusion of the carotid arteries following the accepted general procedure as described in, for example, EP 230 370 and R. Gill, A. C. Foster and G. N. Woodruff, J. Neuroscience, 1987, 7, 3343-3349.

Typical procedures and results are exemplified as follows:

a) Administration of the Test Compound Prior to Induction of Ischaemia.

Ischaemia was induced in gerbils by 10 minute occlusion of both carotid arteries. Restoration of blood flow after occlusion was checked visually and the animals were allowed to survive for 4 days. The extent of neuronal degeneration in the hippocampus was then assessed. The test compounds were administered (i.p.) as a single dose 30 minutes prior to occlusion. Typical results are shown in Table 1. As is seen in Table 1, chlormethiazole was effective in reducing the damage to the CA1/CA2 hippocampal neurones.

TABLE 1

| Test compound | Dose | Number of Animals | % Damage to CA1/CA2 Hippocampal Neurones |
|---|---|---|---|
| None | — | 10 | 94.9 ± 2.0 |
| Chlormethiazole ethanedisulphonate | 100 mg/kg | 7 | <5 |
| Chlormethiazole ethanedisulphonate | 50 mg/kg | 8 | 37.6 ± 13.4 |
| Prior Art Compounds | | | |
| MK 801[a] | 3 mg/kg | 6 | <5 |
| Ifenprodil[b] | 4 mg/kg | 7 | 62 ± 8.0 |

References to Prior Art Compounds
[a]: See, for example, EP 230 370
[b]: See, for example, E. T. MacKenzie, B. Gotti, J-P. Nowicki & A. R. Young (1984) in 'Neurotransmitters and the Cerebral Circulation'. Raven Press, New York, pp 219–243.

b) Administration of the Test Compound Following Induction of Ischaemia.

The general procedure described in (a) above was followed except that the test compound was administered (i.p.) as a single dose at the stated time following the end of the occlusion. No administration was made prior to the occlusion. Typical results are shown in Table 2. As is seen in Table 2, chlormethiazole was effective in reducing the damage to the CA1/CA2 hippocampal neurones when administered after the ischaemic insult.

TABLE 2

| Test compound | Dose | Time of Dosing after Induction of Ischaemia | Number of Animals | % Damage to CA1/CA2 Hippocampal Neurones |
|---|---|---|---|---|
| None | — | — | 9 | 80.4 ± 7.9 |
| Chlormethiazole ethanedisulphonate | 100 mg/kg | 30 minutes | 8 | 12.8 ± 10.4 |
| Chlormethiazole ethanedisulphonate | 50 mg/kg | 30 minutes | 8 | 69.4 ± 6.9 |
| Chlormethiazole ethanedisulphonate | 100 mg/kg | 1 hour | 9 | 14.3 ± 8.7 |
| Chlormethiazole ethanedisulphonate | 100 mg/kg | 2 hours | 8 | 7.25 ± 4.8 |
| Chlormethiazole ethanedisulphonate | 100 mg/kg | 6 hours | 10 | 45.6 ± 14 |

What we claim is:

1. A method for the treatment of neurodegeneration involving loss of neuronal structure following a pathological insult in the brain of a human subject comprising administering to said subject a therapeutically effective amount of 5-(2-chloroethyl)-4-methylthiazole, or a pharmaceutically acceptable salt or solvate thereof.

2. The method according to claim 1, wherein the pathological insult is caused by stroke.

3. The method according to claim 1, wherein the pathological insult is caused by cerebral ischaemia.

4. The method according to claim 1, wherein the pathological insult is caused by hypoxia.

5. The method according to claim 1, wherein the pathological insult is caused by multi-infarct dementia.

6. A method for the treatment of neurodegeneration involving loss of neuronal structure following a pathological insult in the brain of a human subject caused by stroke, cerebral ischemia, hypoxia, or multi-infarct dementia, comprising administering to said subject a therapeutically effective amount of 5-(2-chloroethyl)-4-methylthiazole or a pharmaceutically acceptable salt or solvate thereof, in the dosage range of about 10–1000 mg/kg body weight, in combination with a pharmaceutically acceptable carrier.

7. The method of claim 6 wherein the dosage range is 25–250 mg/kg body weight.

* * * * *